(12) United States Patent
Eddleman et al.

(10) Patent No.: US 6,616,912 B2
(45) Date of Patent: Sep. 9, 2003

(54) BI-COMPONENT MICROPOROUS HOLLOW FIBER MEMBRANE STRUCTURE FOR IN VIVO PROPAGATION OF CELLS

(75) Inventors: Roy T. Eddleman, Los Angeles, CA (US); Jesus Martinez, Rancho Dominguez, CA (US)

(73) Assignee: Spectrum Laboratories, Inc., Rancho Dominguez, CA (US)

( * ) Notice: Subject to any disclaimer, the term of this patent is extended or adjusted under 35 U.S.C. 154(b) by 0 days.

(21) Appl. No.: 09/754,597

(22) Filed: Jan. 5, 2001

(65) Prior Publication Data

US 2002/0090690 A1 Jul. 11, 2002

(51) Int. Cl.$^7$ ............... A61K 49/00; A61F 2/00; C12N 11/04; C12N 5/00; C12N 3/00
(52) U.S. Cl. ............ 424/9.1; 424/9.2; 424/422; 424/424; 424/93.7; 435/182; 435/382; 435/398; 435/400; 435/401; 435/289.1
(58) Field of Search ............... 424/174, 177, 424/180, 182, 289.1, 395, 398, 382, 9.1, 93.7, 9.2, 422, 423, 424; 435/400, 401

(56) References Cited

U.S. PATENT DOCUMENTS

| 4,035,459 A | 7/1977 | Kesting |
| 4,127,625 A | 11/1978 | Arisaka et al. |
| 4,229,154 A | 10/1980 | Chaban, Jr. et al. |
| 4,322,381 A | 3/1982 | Joh |
| 4,323,627 A | 4/1982 | Joh |
| 4,342,711 A | 8/1982 | Joh et al. |
| 4,380,520 A | 4/1983 | Taylor |
| 4,744,932 A | 5/1988 | Browne |
| 5,698,413 A | 12/1997 | Hollingshead |

*Primary Examiner*—David M. Naff
(74) *Attorney, Agent, or Firm*—Edgar W. Averill, Jr.

(57) ABSTRACT

A bi-component microporous hollow fiber membrane structure is provided for in vivo propagation of cells and use in testing of the effect of medical treatments on cells within the structure. The structure has an inner structure fabricated from a first bio-compatible polymer and an outer structure fabricated from a different polymer that has a lower tendency for cell adhesion than the inner structure polymer. In this way, the inner structure can be selected to optimize cell propagation and the outer structure can be fabricated from a polymer which optimizes the removal of the bi-component structure from its implanted location. The inner and outer structures may have a pore size between 10 and 1000 Angstroms and 100 and 2000 Angstroms, respectively, and be formed from polysulfone or polyether sulfone and polyvinyledene difuoride, respectively. The membrane structure can form macrocapsules containing media and living cells for implanting.

6 Claims, 1 Drawing Sheet

BI-COMPONENT MICROPOROUS HOLLOW FIBER MEMBRANE STRUCTURE FOR IN VIVO PROPAGATION OF CELLS

BACKGROUND OF THE INVENTION

The field of the invention is medical testing and the invention relates more particularly to screening the effect of chemotherapeutic agents in vivo using target cells grown in bio-compatible semi-permeable membrane capsules.

A method of evaluating chemotherapeutic agents in vivo is disclosed in U.S. Pat. No. 5,698,413 which is hereby incorporated by reference herein. The method broadly utilizes the encapsulation of target cells, such as tumors, or cells with viral infection within a small capsule, which capsule has a microporous wall. This capsule is then implanted in a living organism. The encapsulation prevents the spread of the tumor or other target cells from within the capsule into the living organism. Such target cells, being larger than the pores of the wall of the capsule, are unable to migrate therethrough to spread the tumor to the host. The pores in the capsule wall, however, are large enough to permit the permeation of the treatment into the interior of the capsule through the cell wall, since the treatment substances are smaller than the openings in the pores of the capsule wall. Then after the living organism has been subjected to appropriate treatment, the capsule is removed and the effect of the treatment on the tumor or other target cell within the capsule can be determined.

In order for the target cell to multiply, it has been found necessary, or at least highly desirable, that the cell be capable of becoming anchored to the inner wall of the capsule. On the other hand, it is undesirable for the outer wall of the capsule to anchor itself unduly to the host, since this makes it difficult to remove for evaluation.

The formulation, fabrication, application of hollow membrane structures are well known in the prior art. Such hollow membrane structures have been used for filtration, purification, and reclamation of industrial waste products. Such microporous members are also used in highly sophisticated bio-medical applications in the health services field. Typical applications include hemodialysis, extracorporeal gas exchange, process filtration of pharmaceutical solutions, and the cultivation and expansion of mammalian cells in bioreactors. Such hollow fiber membranes are most typically made by conventional synthetic fiber spinning methods to provide hollow fiber membrane structures. The spinning methods include melt spinning, dry spinning, wet spinnings, and various combinations thereof. These methods are well illustrated in the following U.S. Pat. Nos. 4,035,459; 4,127,625; 4,229,154; 4,322,381; 4,323,627; 4,342,711; 4,380,520; and 4,744,932.

Various human or animal tumor cell lines and HIV infiltrated cells have been successfully encapsulated and implanted in a host biological model as set forth in U.S. Pat. No. 5,698,413. Polymers used for such encapsulation include polysulfone, polyether sulfone, and polyvinyledene difloride. Unfortunately, the ideal properties for the inner wall of the encapsulation medium differ from the ideal properties desired from the outer wall. The inner wall requires a significant amount of cell adhesion, whereas too much cell adhesion is a disadvantage on the outer wall, since it interferes with the removal of the capsule after completion of the test. Conversely, to provide a polymer which can readily be removed can provide too little adhesion for the encouragement of cell proliferation within the capsule.

It is, thus, an object of the present invention to provide a hollow fiber membrane structure having an inner wall with optimum cell proliferation characteristics and an outer wall with optimum capsule removal characteristics.

BRIEF SUMMARY OF THE INVENTION

The present invention is for a bi-component microporous hollow fiber member structure for use in the in vivo propagation of cells within the structure. The structure has a semi-permeable inner microporous structure fabricated from a microporous bio-compatible polymer, having a pore size of between 10 and 1000 Angstroms but preferably 10–200 Angstroms, and having the property of cell adhesion to the inner surface thereof. A semi-permeable outer porous structure covers the outer surface of the inner microporous structure, and is fabricated from a polymer having a lower tendency to permit cell adhesion than the polymer from which the inner microporous structure is fabricated. Preferred polymers for the inner microporous structure include polysulfone and polyether sulfone. Preferred polymers for the outer microporous structure are polyvinyledene difloride and polypropylene. Preferably, this bi-component structure is formed in a generally tubular shape and heat sealed at intervals to provide compartments containing media and living cells. The heat sealed compartment may then be implanted in a living organism and then used for various purposes, including evaluation of medical treatments.

DESCRIPTION OF THE PREFERRED EMBODIMENTS

Figure 1:
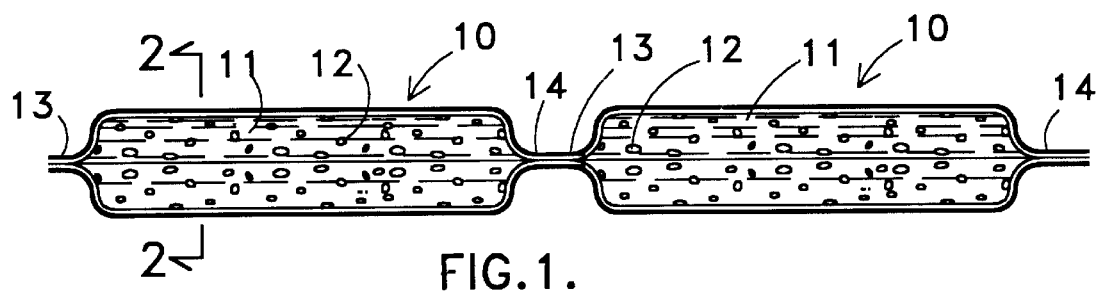
FIG. 1 is a cross-sectional side view of a pair of macrocapsules made from the bi-component membrane structure of the present invention.
Figure 2:
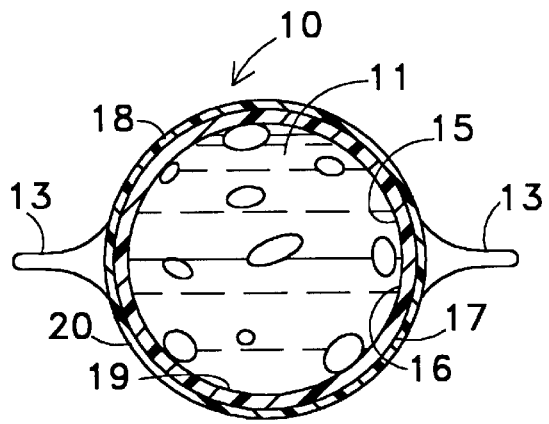
FIG. 2 is a cross-sectional view taken along line 2—2 of FIG. 1.

A pair of macrocapsules 10 are shown in cross-sectional view in FIG. 1. The macrocapsules hold media 11 containing living cells 12. Macrocapsule 10 has a generally tubular wall as shown in FIG. 2. Although the wall is shown as cylindrical, it can of course, be elliptical, generally rectangular, or other hollow shape. Each macrocapsule 10 has a first heat sealed end 13 and a second heat sealed end 14.

The macrocapsule is fabricated for the implantation in a living organism as described in U.S. Pat. No. 5,698,413. When such macrocapsule is so implanted, the living organism in which it is implanted may then be subjected to, for instance, various medical treatments, such as chemotherapy. After treatment, the macrocapsule may be removed and the condition of the cells 12 ascertained. Such testing provides a far more realistic environment than the conventional in vitro evaluation. The cells 12 are larger than the pores in the macrocapsule wall and yet, the pores are large enough to permit the treatment to be absorbed through them. Since cells 12 are encapsulated and incapable of passing through the macrocapsule wall, the organism itself is not infected by the condition of cells 12.

As seen best in FIG. 2, macrocapsule 10 has a semi-permeable inner microporous structure 15 which has an inner surface 16 and an outer surface 17. The inner microporous structure 15 is fabricated from a polymer which permits cell adhesion to the inner surface 16. Cell propagation is enhanced by conditions wherein it adheres to a cell wall. The pore size of inner microporous structure 15 is between 10 and 1000 Angstroms, but preferably 200, and the macrocapsule preferably has an inside diameter between 100 and 1,000 micra, and preferably between 500 and 1,000 micra.

Inner microporous structure 15 is surrounded by a semi-permeable outer microporous structure 18 having an inner surface 19 and an outer surface 20. The outer microporous structure is fabricated from a polymer which has a lower tendency of cell adhesion than the polymer from which the inner microporous structure 15 is fabricated. In this way, the macrocapsule does not have a tendency to become lodged in the living organism in which it is implanted, and may more easily be removed for evaluation. The outer microporous structure should have a pore size also between 100 and 2000 Angstroms, and a preferred polymer for the outer microporous structure is polyvinyledene difloride (PVDF). Preferred polymers for the inner microporous structure include polysulfone and polyether sulfone.

The bi-component microporous hollow fiber member structure may be fabricated from a variety of methods, including co-extrusion, dipping, or sequential extrusion of one hollow fiber structure upon the other. The wall thickness of the macrocapsule should be between 50 and 100 micra and the outer microporous structure may be much thinner than the inner microporous structure since its function is largely to substantially decrease or eliminate the tendency of the macrocapsule 10 to adhere to the tissues of the organism in which it is implanted.

Figure 3:
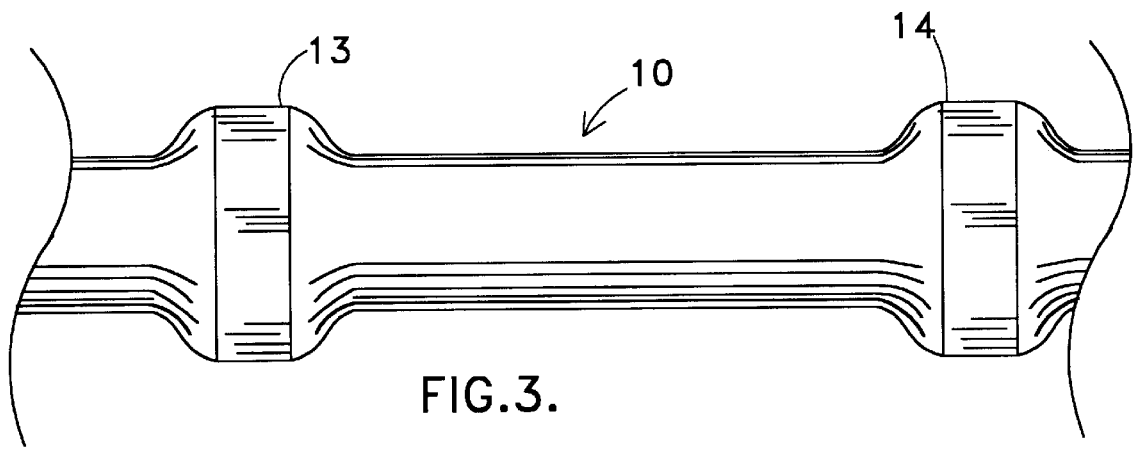
FIG. 3 is a top view of the macrocapsules of FIG. 1.

Various human or animal tumor cell lines and HIV infiltrated cells can be successfully encapsulated and implanted in a host biological model. The polymers from which the macrocapsule is fabricated must, of course, be compatible with biological tissue and provide an ideal environment for cell proliferation and growth, plus subsequent cell harvesting. By providing a two-layer structure, the properties for the inner layer which promote self-proliferation and growth can be enhanced, whereas the outer layer can be selected with different properties which enhance its subsequent removal from the host. The inner microporous structure is preferably spun from a bio-compatible polymer, such as polysulfone or polyether sulfone. The pore size of the inner microporous structure can vary from a useful range of 10 Angstroms to several thousand Angstroms encompassing a molecular weight cut-off from 10,000 Daltons to several million Daltons. The polymer structures used for the inner and/or outer fiber structure can be a single polymer or a co-polymer of any suitable bio-compatible polymer. The bio-compatible polymers are preferably selected from but not limited to those which can be heat sealed to allow for easy to use encapsulation of cell lines, while providing an immunoisolatory function between the host animal model and the encapsulated cells. Once heat sealed as shown in FIG. 3, an individual macrocapsule 10 can be prepared by cutting vertically, as viewed in FIG. 3, the heat sealed portions 13 and 14. The hollow tube before heat sealing is, of course, filled with media 11 and cells 12.

The result is a macrocapsule having optimum inner and outer properties which promote both cell growth within the macrocapsule and subsequent removal after testing.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

We claim:

1. A bi-component microporous hollow fiber membrane structure for use in the in vivo propagation of cells within the structure, said structure comprising:

a semi-permeable inner microporous structure with an inner surface and an outer surface, said semi-permeable inner microporous structure being fabricated from a microporous, biocompatible polymer having a pore size between 10 Angstroms and 1000 Angstroms and having the property of cell adhesion to the inner surface thereof; and a semi-permeable outer microporous structure with an inner surface adjacent said outer surface of said semi-permeable inner microporous structure and said outer microporous structure having an outer surface and being fabricated from polyvinyledene difluoride (PVDF) having a pore size between 100 Angstroms and 2000 Angstroms, said semi-permeable inner microporous structure and said semi-permeable outer micro-structure being joined to form said bi-component microporous hollow fibre membrane structure having an inner surface and an outer surface and a bi-component wall thickness and wherein said outer microporous structure is fabricated from a polymer having a lower tendency to permit cell adhesion than said polymer from which said inner microporous structure is fabricated.

2. The bi-component microporous hollow fiber membrane structure of claim 1 wherein said bi-component structure has a hollow central portion having an inside diameter of at least 100 microns.

3. The bi-component microporous hollow fiber membrane structure of claim 2 wherein said bi-component structure has an inside diameter of at least 500 microns.

4. The bi-component microporous hollow fiber membrane structure of claim 3 wherein said bi-component structure has an inside diameter between about 500 micra and about 1000 microns.

5. The bi-component microporous hollow fiber membrane structure of claim 4 wherein said bi-component wall thickness is between about 50 micra and 100 microns.

6. A bi-component microporous hollow fiber membrane structure for use in the in vivo testing of the effect of medical treatment on cells within the structure, said structure comprising:

a semi-permeable inner microporous structure with an inner surface and an outer surface, said semi-permeable inner porous structure being fabricated from a microporous, biocompatible polymer having a pore size between 10 Angstroms and 1000 Angstroms fabricated from a polymer selected from the group consisting of polysulfone and polyether sulfone; and a semi-permeable outer microporous structure with an inner surface adjacent said outer surface of said semi-permeable inner microporous structure and said outer microporous structure having an outer surface and being fabricated from polyvinyledene difluoride (PVDF) having a pore size between 100 Angstroms and 2000 Angstroms, said semi-permeable inner microporous structure and said semi-permeable outer micro-structure being joined to form said bi-component microporous hollow fibre membrane structure having a bi-component inner surface and a bi-component outer surface and a bi-component wall thickness.

* * * * *